US006248130B1

(12) United States Patent
Perry

(10) Patent No.: US 6,248,130 B1
(45) Date of Patent: Jun. 19, 2001

(54) PEGS FOR ORBITAL IMPLANTS

(76) Inventor: Arthur C. Perry, 16418 La Via Feliz, Rancho Santa Fe, CA (US) 92067-1102

( * ) Notice: Subject to any disclaimer, the term of this patent is extended or adjusted under 35 U.S.C. 154(b) by 0 days.

(21) Appl. No.: 09/366,447

(22) Filed: Aug. 3, 1999

Related U.S. Application Data

(60) Division of application No. 08/853,647, filed on May 9, 1997, now Pat. No. 6,033,437, which is a continuation-in-part of application No. 08/241,960, filed on May 12, 1994, now abandoned, which is a continuation of application No. 07/768,502, filed on Sep. 30, 1991, now abandoned, said application No. 08/853,647, is a continuation-in-part of application No. 08/660,095, filed on Jun. 6, 1996, now abandoned, which is a division of application No. 08/241, 960, filed on May 12, 1994, now abandoned, which is a continuation of application No. 07/768,502, filed on Sep. 30, 1991, now abandoned.

(51) Int. Cl.[7] ............................................. A61F 2/14
(52) U.S. Cl. ............................................. 623/6.64
(58) Field of Search .................. 623/6.64, 4.1; 427/2.24

(56) References Cited

U.S. PATENT DOCUMENTS

| Re. 34,307 | 7/1993 | Perry ..................... 623/11 |
| 2,688,139 | * 9/1954 | Jardon ................... 623/6.64 |
| 3,896,196 | 7/1975 | Dickey et al. ............. 264/6 |
| 3,986,212 | 10/1976 | Sauer ..................... 3/1.91 |
| 4,007,494 | 2/1977 | Sauer ..................... 3/1.9 |
| 4,213,816 | 7/1980 | Morris ................... 156/245 |
| 4,256,845 | 3/1981 | Morris et al. ............. 521/61 |
| 4,307,472 | 12/1981 | Morris ................... 3/1 |
| 4,321,711 | 3/1982 | Mano ..................... 3/1.4 |
| 4,904,259 | 2/1990 | Itay ...................... 623/16 |
| 4,925,924 | 5/1990 | Silver et al. ............. 530/356 |
| 4,976,731 | * 12/1990 | Perry ..................... 623/4 |
| 4,976,736 | 12/1990 | White et al. ............. 623/16 |
| 5,002,582 | * 3/1991 | Guire et al. ............. 623/66 |
| 5,026,392 | * 6/1991 | Gordon ................... 623/6.64 |
| 5,089,021 | * 2/1992 | Vachet ................... 623/6.64 |
| 5,192,293 | 3/1993 | Cartwright et al. ........ 606/172 |

(List continued on next page.)

FOREIGN PATENT DOCUMENTS

| 2704422 | 11/1994 | (FR) . |
| WO98/0739 | 2/1998 | (WO) . |

OTHER PUBLICATIONS

Ophthalmic Plastic and Reconstructive Surgery, vol. 10, No. 2, pp:96–103, "Comparison of Fibrovascular Ingrowth into Hydroxyapatitte and Porous Polyethylene Orbital Implants", P.A.D. Rubin,M.D., et al.

(List continued on next page.)

Primary Examiner—David J Isabella
Assistant Examiner—Urmi Chattopadhyay
(74) Attorney, Agent, or Firm—Henri J. Acharmasson; John D. Buchaca

(57) ABSTRACT

An orbital implant motility peg capable of being placed in vivo in an orbital implant, wherein the peg is configured to permit rotation about a longitudinal axis of the peg during or following insertion of the peg into the implant, and wherein the peg comprises a means for removable attachment to an artificial eye. The means for removable attachment can comprise a convex surface capable of articulating with a concave surface on the artificial eye. The means for removable attachment can comprise a ball capable of providing a ball of a ball-and-socket articulation. The peg can contain a means for removable attachment that comprises a positive or a negative magnetic pole. The peg can define a cavity capable of containing a stint for attachment to an artificial eye. Also disclosed is a stint capable of being placed in such a peg cavity. The stint can comprise a means for removable attachment to an artificial eye such as a ball of a ball-and-socket articulation. Also disclosed are related prosthetic complexes and related methods.

39 Claims, 3 Drawing Sheets

U.S. PATENT DOCUMENTS

| | | | | |
|---|---|---|---|---|
| 5,192,315 | * | 3/1993 | Jacob-LaBarre | 623/6.64 |
| 5,306,302 | | 4/1994 | Bauer et al. | 623/16 |
| 5,326,356 | | 7/1994 | Della Valle et al. | 623/15 |
| 5,330,529 | | 7/1994 | Cepela | 623/4 |
| 5,348,788 | | 9/1994 | White | 428/131 |
| 5,433,748 | | 7/1995 | Wellisz | 623/10 |
| 5,466,258 | | 11/1995 | Rubin | 623/4 |
| 5,466,259 | * | 11/1995 | Durette | 623/4 |
| 5,522,887 | | 6/1996 | Hoe | 623/4 |
| 5,522,888 | | 6/1996 | Civerchia | 623/4 |
| 5,556,427 | | 9/1996 | Durette | 623/4 |
| 5,571,139 | | 11/1996 | Jenkins, Jr. | 606/232 |
| 5,843,185 | | 12/1998 | Rolden et al. | 623/5 |
| 5,856,367 | | 1/1999 | Barrow et al. | 521/64 |
| 5,876,435 | | 3/1999 | Swords et al. | 623/4 |
| 5,876,446 | | 3/1999 | Agrawal et al. | 623/11 |
| 6,001,895 | * | 12/1999 | Harvey et al. | 523/113 |

OTHER PUBLICATIONS

"A Screw–Type Implant", T.I. Moore, M.D., pp: 1–5.

Plastic and Reconstructive Surgery, vol. 88, No. 6, 12/91, "Response of Porous Hydroxyapatite to Contiguous Tissue Infection", pp:1076–1080.

Ophthalmology, vol. 99, No. 5, 5/92, pp: 824–830, Role of Magnetic Resonance Imaging in the Evaluation of the Hydroxyapatite Orbital Implant.

Experimental Eye Research, vol. 54, No. 6, 6/92, pp: 387–998, "Recombinant Human Basic Fibrobalst Growth Factor (RH–bFGF) in Three Different Wound Models of Rabbits: Corneal Wound Healing Effect and Pharmacology", P. Riec et al.

Current Eye Research, vol. 11, No. 12, 12/92, pp: 1161–1172, "Human Recombinant bFGF Stimulates Corneal Endothelial Wound Healing in Rabbits", P. Rieck, et al.

JNM, vol. 34, No. 3, 3/93, pp: 467–468, "Evaluation of Biomatrix Hydroxyapa Ocular Implants with Technetium–99–m–MDP", D. Baumgarten et al.

Ophthalmic Plastic and Reconstructive Surgery, vol. 10, No. 2, 6/94, pp: 96–103, "Comparison of Fibrovascular Ingrowth into Hydrosyapatite and Porous Polyethylene Orbital Implants", P.A.D. Rubin, M.D. et al.

Transactions of the Amer. Ophthal. Soc., 129TH Annual Meeting, 1993, pp: 177–189,"Lack of Complications of the Hydroxyapatite Orbital Implant in 250 Consecutive Cases", C. L. Shields, M.D., et al.

Proc. Natl. Acad. Sci. USA, vol. 83, pp;7297–7301, 10/86, Basic Fibroblast Growth Factor Induces Angiogenesis In Vitro, R. Montesano et al.

Amer. Assoc. for Advan. of Science, vol. 235, pp: 400–447 "Angiogenic Factors", J. Folkman et al.

CRC Critical Reviews in Biocompatibility, vol. 4, Issue 1, 44–76 (Contents) Peptide Growth Factors and Their Receptors I, Chapter 7, pp: 369–417, "Fibroblast Growth Factors", A. Baird, et al.

Ophthalmic Plastic and Reconstructive Surgery, vol. 7, No. 1, 3/91, pp: 8–22, Orbital Augmentation by Hydroxylapatite–Based Composites, A Rabbit Study and Comparative Anaysis, G.E. Geist, M.D. et al.

Amer. Journal of Ophthalmology, E. Jackson, vol. 32 1949 pp:78–89.

Plastic Eye Implant, A.D. Ruedemann, M.D. pp: 947–952.

A Positive Contact Ball and Ring Implant for Use After Enucleation, N. L. Cutler, M.D. pp: 73–81.

Clinical Orthopaedics, No. 23, The Use of Plaster of Paris to Fill Defects in Bone, L.F. Peltier, M.D., Ph.D. pp:1–31.

"The Evolution of the Ocular Motility Implant" H. P. Gougelmann pp: 689–711.

J. Biomed. Mater Res. vol. 10 pp: 311–322; An Evaluation of Bone Growth into Porous High Density Polyethylene, J.J. Klawitter et al.

Journal of Biomedical Materials Research, vol. 13, No. 1, 1/79, pp:101–108, Implant Site Infection Rates with Porous and Dense Materials, K. Merritt et al.

Transactions of the Ophthalmological Society of the U.K., vol. 5, Evisceration of the Globe, with Artificial Vitreous, P.H. Mules pp: 200–206.

* cited by examiner

PEGS FOR ORBITAL IMPLANTS

CROSS-REFERENCE TO RELATED APPLICATIONS

This application is a divisional of U.S. application Ser. No. 08/853,647 filed May 9, 1997, now U.S. Pat. No. 6,033,437 Mar. 7, 2000 which is a continuation-in-part of U.S. application Ser. No. 08/241,960 filed May 12, 1994 now abandoned, which is a file wrapper continuation of U.S. application Ser. No. 07/768,502 filed Sep. 30, 1991 now abandoned. U.S. Ser. No. 08/853,647 is also a continuation-in-part of U.S. application Ser. No. 08/660,095 filed Jun. 6, 1996 now abandoned, which was a divisional of U.S. application Ser. No. 08/241,960 filed May 12, 1994 now abandoned, which was a file wrapper continuation of U.S. application Ser. No. 07/768,502 filed Sep. 30, 1991 now abandoned. Each of the above-applications is fully incorporated by reference herein, and their priority is claimed.

FIELD OF THE INVENTION

This invention relates to prosthetic organs. More particularly, it relates to materials for attaching an artificial eye to an integrated orbital implant. It also relates to materials and methods for use in conjunction with orbital or ocular implants.

BACKGROUND OF THE INVENTION

Enucleation or evisceration of the eye is performed because of disease or trauma that make the removal of the eye, or the intraocular contents of the eye, necessary. Following such a procedure, the patient normally desires use of an artificial eye to restore a more normal appearance. To satisfactorily fit an artificial eye into the orbital socket, an orbital (herein also called an "ocular") implant must be placed within the orbit to replace the volume that was lost when the eye or its contents was removed. However, the use of an orbital implant and the subsequent fitting of the artificial eye confer more than a cosmetic benefit. They help maintain the normal structure of the eyelids and eyebrows; they aid in normal tear drainage; and, when used in children, they help stimulate normal growth of the orbital bones.

Even though an artificial eye can be made which has a very realistic appearance, prior to the present invention such artificial eyes have failed to track in conjunction with the normal eye because there was no coupling between the artificial eye and the orbital implant. The artificial eye drifted within the socket and did not track with the normal eye. This lack of tracking was quite apparent and disconcerting to even a casual observer, creating a sense of self-consciousness on the part of the patient. Because of this shortcoming of traditional implants, efforts have been made to attach the eye muscles to the implant and then to attach the artificial eye to the implant. This provided adequate tracking of the artificial eye. However, the success was short-lived because, in a brief period of time, the implant was extruded from the orbit. This implant extrusion occurred because the fixing of the artificial eye to the implant material exposed the implant to the outside environment. This permitted bacteria to enter, and the implant became chronically infected. This exposure was considered necessary, however, to produce an attachment between the implant and the artificial eye.

A wide variety of other materials have been used for orbital implants, such as ivory spheres, gold globes, silk, catgut, acrylic plastics or silicones, human bone (G. C. Sood et al., *International Surgery*, (1970) Vol. 54, No. 1, p. 1); and antigen-free cancellous calf bone, so called "Kiel Bone," (A. C. B. Molteno, et al., *Brit. J. Ophthal.*, (1973) Vol. 57, p. 615 and A. C. B. Molteno, *Trans: of the Ophthal. Soc. New Zealand* (1980) Vol. 32, p. 36. These other materials, however, did not provide for significant integration of tissue and vascularization of the implant itself. As described in U.S. Pat. No. 4,976,731, these materials which did not permit significant integration of tissue were disadvantageous in that, when the surrounding tissue heals, the patient risked chronic infection as a result of subsequent procedures necessary to connect the implant to the artificial eye so as to provide tracking of the artificial eye. Also, the weight of the artificial eye was not supported by the implant. This lack of support puts pressure on the lower lid causing lower lid sagging.

A porous orbital implant overcomes these problems. One type of porous orbital implant is described in U.S. Pat. No. 4,976,731. U.S. Pat. No. 4,976,731 issued Dec. 11, 1990 in the name of the inventor herein, Arthur C. Perry; this patent is incorporated by reference in its entirety. The term integrated is used to denote a porous structure capable of containing fibrovascular ingrowth into its pores whether or not such ingrowth has occurred. In the U.S. Pat. No. 4,976,731 patent, the use and preparation of an orbital implant comprising hydroxyapatite is described. The use of porous hydroxyapatite allows integration of the implant with fibrovascular tissue. These porous hydroxyapatite implants ("PHA" implants) are described in the U.S. Pat. No. 4,976,731 patent, as providing advantages over other implant materials particularly because such integration of the patient's own tissue allows coupling of the implant to the artificial eye, as well as increased long-term stability of both the artificial eye and the implant.

In the past, unevenly textured surfaces of orbital implants have required coating so that the surface is smooth and slippery, so as to allow for facile insertion of the orbital implant into the eye socket. Uneven or roughly textured surfaces, such as the surface of a hydroxyapatite orbital implant, may cause trauma to or otherwise tear tissue surrounding the eye socket where the implant is to be inserted. An uneven or rough textured surface does not allow the implant to be placed deeply into the orbital socket. This problem has been addressed by using homologous or autologous materials, such as human or animal sclera, fascia, or dura for a coating. See, U.S. Pat. No. 4,976,731 which describes, for example, the use of the patient's own scleral sac in the case of an eviscerated eye (in which all the inner contents of the eye have been removed). If the eyeball has been enucleated (removal of the entire eyeball after severing it from the eye muscles and the optic nerve), other material must be used for coating the orbital implant. Materials such as scleral sacs obtained from cadavers or from eye banks, collagen tissue obtained from tissue banks or from animals, or autologous tissue, from another area of the patient's own body have been used.

These coating materials may be difficult to obtain or use. For example, scleral sacs obtained from eye banks may be unavailable in some geographic locations. Moreover, these materials may facilitate the transmission of human or animal disease. Human tissues, in particular, may be capable of transmission of such disease as hepatitis or Acquired Immune Deficiency Syndrome (AIDS). Moreover, some of these materials are perishable, and thus must be transported rapidly and used rapidly. If autologous tissue is used, there is, of course, a certain amount of trauma to the patient himself because another invasive operation is required.

Typically with the use of human or animal tissue for coating orbital implants, the surgeon must perform such wrapping immediately prior to the implantation, thus, the time of surgery is lengthened and the time the patient must be under anesthesia is prolonged. Accordingly, large-scale production of pre-coated orbital implants has been impracticable and unavailable.

As a result of the shortcomings of prior implants, there also exists a need for means to improve the vascularization of integrated orbital implants. As set forth above, integrated orbital implants, for example, those comprised of hydroxyapatite, allow vascularization of the implant itself. In a certain percentage of the patients (about three to five percent), however, vascularization is impeded or inhibited for no known reason. In addition, an increased rate or degree of vascular integration into the orbital implant may benefit patients by allowing a faster fitting of an artificial eye.

The advantages to improved vascularization, either in terms of rate of penetration, or the density of blood vessels formed per unit volume, are clear: means to attach the orbital implant to the artificial eye (and thereby provide means for smooth movement of the artificial eye) may occur sooner; and, the strength of the coupling of the orbital implant to the surrounding muscle and scar tissue may be enhanced. With increased vascularization, implant migration and extrusion is decreased. Integration of the tissue is extremely important to properly hold the implant in place.

Concerning coating materials for orbital implants, there is an unmet and long felt need for an orbital implant coating material which is not capable of disease transmission, which causes no detriment or undue trauma to the recipient of the orbital implant, which can be stored and used later without significant problems of perishability, which can be practicably produced in conjunction with the orbital implant itself, which does not lengthen the operation or unduly prolong the time the patient is anesthetized, and which provides a smooth, even surface for the orbital implant.

Therefore, there also exists a need for improved means for vascularization of integrated orbital implants. This improved means for vascularization may be associated with the orbital implant coating, or associated with the orbital implant itself or, as an ongoing therapy.

SUMMARY OF THE INVENTION

As used herein, orbital implant is synonymous with ocular implant. The term "integrated" is used herein to denote those implants into which the orbital tissue of the recipient is capable of penetrating. Also as used herein, the term "coat" or "coating" denotes material which is used to cover the implant. One type of "coating" is a non-liquid form of material, such as a sheet-like bio-polymer (described in further detail herein), which is here also described as something which is "wrapped" or a "wrapping."

The present invention provides for novel improvement of orbital implants by providing synthetic coating materials. Also, means for coating integrated orbital implants so that the implant surface is smooth is herein provided. Relatedly, means for improved vascularization of integrated orbital implants are provided. Compositions and methods are described herein.

Synthetic coating materials are provided which virtually eliminate the risk of disease transmission previously resulting from use of human or animal tissues. Also, a synthetic coated implant provides for a decrease in preparation time since the orbital implant does not require the surgeon to coat the orbital implant immediately prior to insertion into a patient. This also reduces operative time and time under anesthesia. In addition, the use of synthetic materials eliminates morbidity caused by use of the patient's own tissue, as well as the problems caused by the perishable nature of naturally occurring products.

There is thus provided a means for a uniform surface which enables an orbital implant, whether integrated or non-integrated, to freely slide into the orbital socket with minimal damage to the surrounding tissue. As an additional benefit, the use of synthetic materials may improve the rate or robustness of vascularization of integrated orbital implants. One example provided herein is coating a hydroxyapatite integrated orbital implant with Plaster of Paris. Other examples include bio-polymers. Again, these materials may be suitable for dipping the implant, or may be in solid (or semi-solid) form, and may be suitable for wrapping the implant. This also satisfies the need for an implant which may be deeply inserted into the orbital socket, yet permits fibrovascular integration.

Relatedly, provided are means and compositions for improved vascularization of the orbital implant. This improved vascularization can comprise addition of vascularizing agents to the orbital implant, or to the coating materials. These agents promote vascularization of the orbital implant via enhancing the vascularization process from the surrounding tissue. Other advantages to using vascularizing agents may include improved wound healing or other secondary therapeutic benefits to the patient. There is thus provided the inclusion of vascularizing agents either in association with the orbital implant, in association with the coating material, or via the addition of exogenous vascularizing agents at the time of the insertion of the orbital implant, or as an ongoing therapy until the orbital implant is sufficiently integrated.

Also disclosed is an orbital implant motility peg comprising a means for removable attachment to an artificial eye or a component of an articulation at a distal end thereof. The peg can be configured to permit rotation of the peg itself or an artificial eye associated therewith, relative to a longitudinal axis of the peg; the rotation can occur during or following insertion of the peg into an orbital implant. Methods of using such pegs are disclosed.

Set forth below are the preferred embodiments. These embodiments are illustrative, and are not intended to be limitations to the appended claims.

DESCRIPTION OF THE PREFERRED EMBODIMENTS

Figure 1:
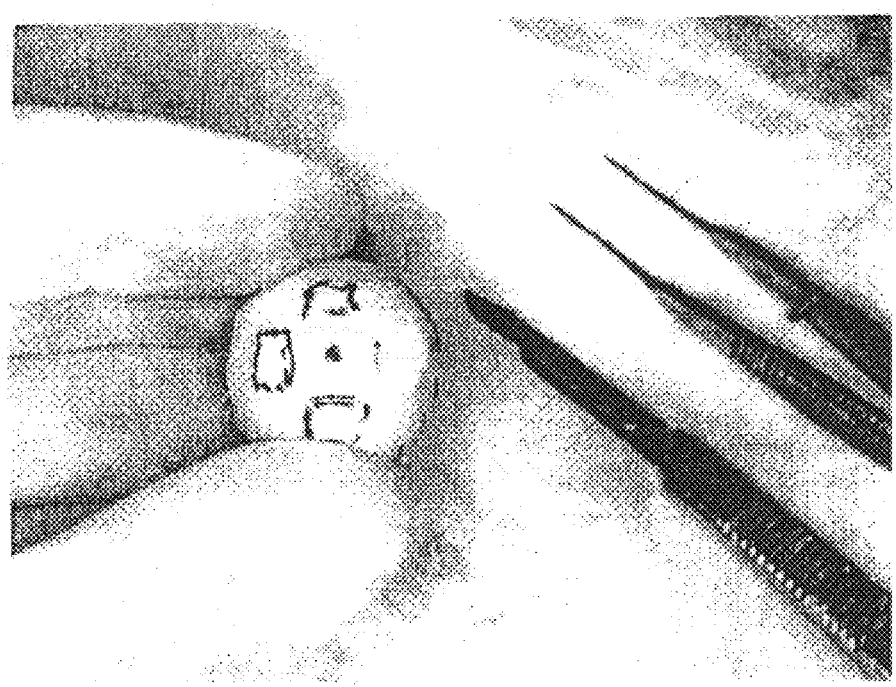
FIG. 1 is a photographic representation of a porous hydroxyapatite implant wrapped in sclera with windows cut into the sclera for attachment of muscles and for in-growth of vessels. Similar windows may be cut in suitable synthetic coating or wrapping materials.

Orbital Implants and Prosthetic Complexes:

The preferred implant is an integrated orbital implant. As set forth above, the term "integrated" herein denotes those implants into which the recipient's own tissue will penetrate as the socket surrounding the implant heals. Other implants which are not "integrated," such as certain acrylic or silicone implants, may also be used, and one skilled in the art will recognize the extent to which the structures, compositions and methods described herein are applicable thereto.

Low density, porous hydroxyapatite of the kind obtained from coral or by synthetic means is a preferred material for the integrated orbital implant. Implants made of low density, porous hydroxyapatite are available from Integrated Orbital Implants, Inc., San Diego, Calif. A less preferred material is granular high density hydroxyapatite, such as that used as bone grafting material. For low density hydroxyapatite, spheres were machined to appropriate sizes to be used as implants from a larger block of porous hydroxyapatite. The hydroxyapatite implants were sterilized, preferably by autoclaving, prior to being used in the surgical procedures described herein.

As noted above, orbital implants may be used in eviscerations, where the contents of the eyeball are removed; in this context the coating or wrapping was typically provided by the patient's own scleral sac which was sewn closed around the implant. For enucleation, where the entire eyeball is removed (after severing it from the eye muscles and the optic nerve); the implant may be placed inside coating material which may be sutured closed, or the implant may be dipped in coating material.

In addition, the present compositions and procedures were useful for replacing original orbital implants with a second orbital implant. This "secondary" replacement is particularly important as some patients may desire to replace their original non-integrated implant with an integrated orbital implant so as to achieve more natural movement, and more natural eye position. This replacement with an additional implant may also be required if the previous implant has migrated, has become exposed, or has been extruded. For secondary implant replacement, if desired, the implant is placed inside coating material which may be closed via suturing (if appropriate), or the implant may be dipped in coating material prior to use. In the above surgical procedures, the implant or, if coated, the coated implant may then be sutured to the patient's extraocular muscles of the orbit.

Generally, after implantation of an integrated orbital implant, the socket was allowed to heal for approximately six months. During the healing process, fibrovascular tissue penetrates the porous structure of the sphere as the coating material is gradually absorbed or penetrated. After sufficient in-growth of fibrovascular tissue, the implant can be drilled or otherwise modified to permit an artificial eye to be coupled to it.

U.S. Pat. No. 4,976,731, issued to the present inventor herein, sets forth two embodiments for connecting an orbital implant to an artificial eye. In one embodiment, the artificial eye is permanently fitted with a peg which then fits into a hole drilled into the implant, thus coupling the implant with the artificial eye. In another embodiment, a protruding peg is placed into a drilled hole of the implant and the artificial eye is recessed to receive the peg and thus be coupled with the implant via the peg. In either embodiment, the artificial eye and peg can be readily removed for therapeutic purposes. One skilled in the art will recognize other means to attach the artificial eye to the implant which has integrated.

For example, where a peg was placed into a drilled hole of the implant and the artificial eye comprises a recess to receive the peg, the distal end of the peg could be essentially round in cross-section so that there is rotation around a longitudinal axis of the peg. As appreciated by one of ordinary skill in the art, other mechanisms for achieving rotation relative to a longitudinal axis of the peg can also be used. Furthermore, there is preferably movement of the artificial eye in three dimensions, with rotation about the longitudinal axis of te peg ("the z axis") and movement along "x" and "y" axes of a plane perpendicular to the z axis.

For example, movement of the artificial eye relative to the peg has been achieved by a smooth convex peg surface that mates with a corresponding smooth concave surface on the posterior surface of an artificial eye; these convex and concave surfaces can interact to constitute a ball-and-socket articulation, i.e., a joint or coupling. A ball-and-socket peg embodiment permitted artificial eye movement in three dimensions. Movement of the artificial eye in three dimensions is preferred, since stresses or tension on the artificial eye were eliminated that would otherwise have caused the artificial eye to gap off of the underlying tissues at the extreme limits of gaze.

One embodiment of a ball-and-socket articulation comprises a socket that has an entry aperture that has a slightly smaller diameter than the diameter of the "ball" at the distal end of the peg. This embodiment is referred to as a "locking socket." The shape and volume of the socket accommodated the ball once the ball was pushed through the aperture. The "ball" had a lateral area that was held in place by the undermined areas of the "socket" adjacent the aperture, thereby creating the "locking" socket. The ball was generally removable from the socket by performing a reverse of the steps for insertion. Alternatively, a ball-and-socket articulation that has a locking socket configuration was prepared by using a barrel-shaped bit to drill the posterior surface of the artificial eye; once the bit had created an aperture and ground below the posterior surface of the artificial eye, the bit was rocked from side to side to undermine areas lateral to the aperture. In a further alternative, the locking socket was created by use of a second smaller bit that was inserted through the aperture created by a first bit; the smaller bit was then used to undermine the lateral areas.

A locking ball-and-socket embodiment is preferred as it permits movement of the artificial eye in three dimensions and also provides support for the eye. The support provided by a locking socket can prevent an artificial eye from falling out of the orbit of a patient with shallow fornices.

One additional means of coupling the implant to the artificial eye is the use of magnets. For example, one pole of the magnet (for example, the "+" pole) is incorporated within a hydroxyapatite orbital implant. The opposite pole of the magnet (in this example, the "−" pole) is incorporated within the artificial eye. The attraction between poles causes the artificial eye to be coupled to the implant.

Figure 5:
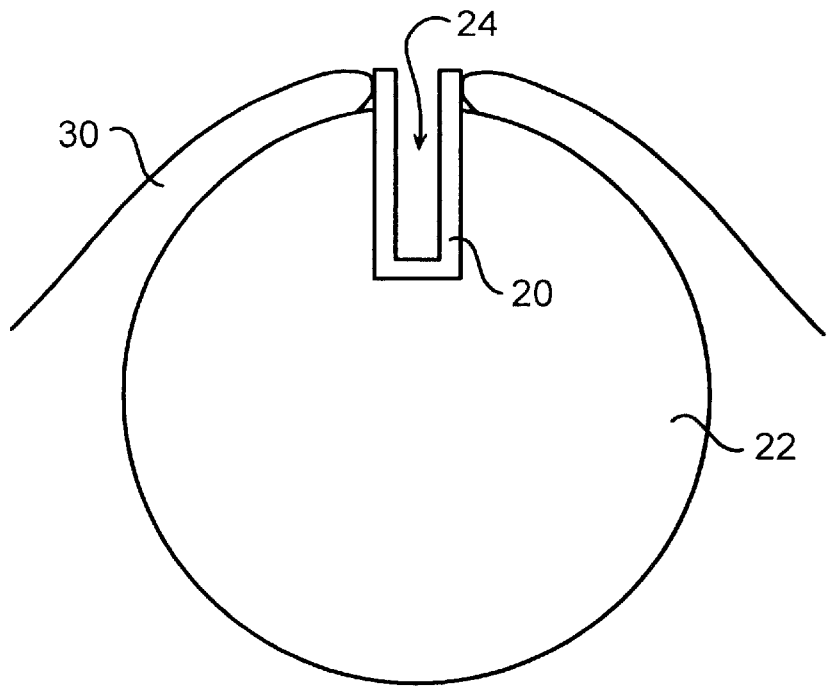
FIG. 5 is a representation of an alternative embodiment of a peg for coupling of an artificial eye to an orbital implant.

An alternative embodiment for attaching an artificial eye to an implant is illustrated in FIG. 5. In this embodiment, a peg 20 in the shape of a closed ended sheath was placed into a hole/recess in an integrated orbital implant 22. As illustrated, the peg protrudes from the surface of the implant a distance approximately a distance equal to the thickness of the overlaying conjunctival tissues. For the embodiment depicted in FIG. 5, a hole was drilled in an implant after sufficient time for fibrovascular ingrowth had occurred. The peg was then placed into the hole. The patient was then allowed to heal for a time sufficient to allow orbital tissue 30

(epithelial or fibrovascular) to grow between the peg and the walls of the hole. In this embodiment of peg 20, the peg defines a cavity 24 into which orbital tissue 30 does not grow.

Figure 6:
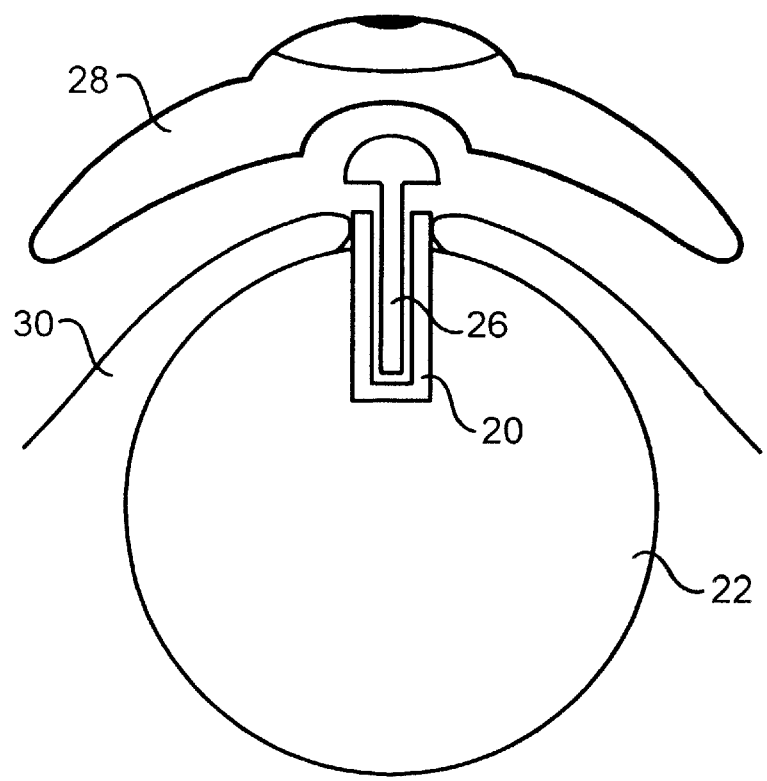
FIG. 6 depicts a sheath-like embodiment of the peg with a stint placed therein, and that the stint is permanently attached to an artificial eye.

FIG. 5 depicts a cross-section of an integrated orbital implant after it has been drilled and a peg placed therein. Preferred materials for a peg of the embodiment depicted in FIG. 5 are biocompatible and include polymers and metals. Referring now to FIGS. 5 and 6, cavity 24 defined by peg 20 was capable of containing a stint 26. An advantage of this peg embodiment is that human tissue is not regularly contacted during the insertion or removal of the stint. Thus, by use of this embodiment, trauma to delicate orbital tissues was minimized or avoided, and patency of the peg hole was maintained when the peg was removed. For example, in other embodiments during short-term removal of a peg, the tissues lining the implant hole can swell making peg reinsertion difficult, during longer-term peg removal, tissues can grow into and occlude the peg hole.

Stint 26 can be permanently attached to an artificial eye, or as appreciated by one of ordinary skill in the art can contain a mechanism at its distal end to provide for removable attachment to an artificial eye. For example, the distal end of the stint can comprise a smooth convex surface that mates with a corresponding smooth concave surface on the posterior surface of an artificial eye 28. In one embodiment, the distal end of the stint peg was essentially round in a cross-section perpendicular to a longitudinal axis of the peg, so that there was rotation of the artificial eye around a longitudinal axis of the stint. As appreciated by one of ordinary skill in the art, other mechanisms for achieving rotation relative to a longitudinal axis of the stint can also be used.

Furthermore, there was preferably movement of the artificial eye in three dimensions: with rotation about the longitudinal axis of the stint ("the z axis") and movement along "x" and "y" axes of a plane perpendicular to the z axis. For example, movement of the artificial eye relative to the stint has been achieved by a smooth convex stint surface that mates with a corresponding smooth concave surface on the posterior surface of an artificial eye; these convex and concave surfaces can interact to constitute a ball-and-socket articulation, such as illustrated in FIG. 6. A ball-and-socket embodiment has permitted artificial eye movement in three dimensions relative to the stint. As noted above, movement of the artificial eye in three dimensions is preferred.

One embodiment of a ball-and-socket articulation between an artificial eye and stint can comprise a socket that has an entry aperture that has a slightly smaller diameter than the diameter of the "ball" at the distal end of the stint. This embodiment is referred to as a "locking socket." The shape and volume of the socket accommodated the ball once the ball was pushed through the slightly smaller aperture. A ball-and-socket articulation that has such a socket configuration was prepared by using a barrel shaped bit to drill the posterior surface of the artificial eye; once the bit had created an aperture and had ground below the posterior surface, the bit was rocked from side to side to undermine areas lateral to the aperture, or a second smaller bit was inserted through the aperture and the smaller bit was used to undermine the lateral areas.

In accordance with the present invention, the resulting integrated implants were very satisfactory from the patient's point of view. The implant resisted extrusion from the orbit. Instead, it became an integral part of the orbital structure, because of the integration of the fibrovascular tissue into the porous material. Being fixed to the eye muscles, the implant was capable of tracking with the normal eye. When an artificial eye was fixed to the implant to complete the prosthesis, a very satisfactory, natural appearance results.

To date, over 35,000 patients have had porous hydroxyapatite orbital implants implanted into their orbits. In patients with vascularized implants, there have been no chronic infections or extrusions of the implant, where these patients have been followed up to 11 years.

In those patients who have had the hole drilled into the implant so that it was coupled to the artificial eye, the tracking has been very satisfactory.

Coating Materials:

Preferred coating materials for use with integrated orbital implants satisfy two criteria: (1) they will be accepted by the patient, and not cause undue adverse immune response; and (2) ultimately, upon the integration of the orbital implant, the coating material will be absorbed or penetrated by the patient's body. The term "synthetics" is used herein to denote that the source of material is manufactured in some way, rather than obtained directly from human or other animal sources (such as tissue from the patient himself or eye banks or tissue banks). For example, Plaster of Paris or similar calcium-containing materials are appropriate synthetic coating materials. Materials produced in vitro, such as, for example, by recombinant nucleic acid technology or by cell culture techniques, are herein considered synthetic, as are other more traditional means for chemical synthesis. For example, a gene encoding a polymer, such as collagen, or a subunit thereof, may be expressed in cell culture. Also, animal tissue, or substances obtained from animals are considered synthetic in that such materials must be obtained from animal sources and treated for use in humans.

Preferably, the coating material is a biodegradable, polymeric compound. The term "polymeric" or "polymer" is used here to denote any molecule which comprises a repeated subunit, including proteinaceous molecules. The term "polymeric compound" refers to a compound which contains at least one polymer. The polymer may be cross-linked, and is preferably elastomeric, as opposed to rigid in structure.

Several biodegradable polymers are currently being investigated for medical applications, such as polyglycolic acid, polylactic acid, polycaprolactone, polydioxanone, polycyanoacrylates, polyorthoesters, poly(gamma-ethyl glutamate), as well as pseudo poly(amino acids). For background on the suitability of these polymers for synthetic coating materials in view of the present disclosure, see Kohn, *Medical Designs and Material* (March 1991):25–30, which is herein fully incorporated by reference.

In the case of integrated orbital implants, the coating material is preferably absorbed by the body because any artificial material left in the body may inhibit epithelialization and may become a site of chronic infections Preferably, the outer coating material should be thick enough to make the implant smooth, typically about $\frac{1}{16}$th of an inch thick. In addition, the coating material should otherwise allow for the free formation of fibrovascular tissue within the orbital implant. For example, synthetic extracellular matrix proteins, such as the collagens, or other polymers which provide for structural integrity are also suitable as coating or wrapping materials.

One should recognize that the above materials are illustrative of the present synthetic coating materials, and are not intended as an exhaustive list. Other synthetic coating materials will be apparent to one skilled in the art.

The coating material itself should be sterilized, either in conjunction with the orbital implant, or separately and then used to cover the separately-sterilized implant under sterile conditions. Antibiotics may be used as an additional precaution to prevent infection. The choice of sterilization means will depend, in part, on the coating material used. For example, autoclaving may be inappropriate for various polymers, including proteinaceous compounds, as the extreme temperature and pressure may cause a change in the characteristics of the material. One skilled in the art will be able to readily ascertain which sterilization processes are appropriate for which coating materials/orbital implant materials.

Preferably, the coating material is suitable for covering the implant as part of a single manufacturing process. This is beneficial to surgeons, who save time by not having to prepare the implant immediately prior to placing the implant into the patient. This also benefits patients who are assured of proper implant characteristics, such as lack of immunogenicity, and ready absorption by the body, for example. Additionally, both surgeons and patients benefit, because this embodiment decreases the time during which the patient is under anesthesia. This also benefits the manufacturers who are able to place the implant in the synthetic coating as part of the manufacturing process and are able to store and ship inventory as a single unit. Alternatively, the manufacturer can ship the coating and the implant as two separate units which are then assembled by the surgeon.

For example, the synthetic coating material can be in solution or liquid form. The non-coated implant may be dipped directly into the coating material. Alternatively, the synthetic coating material may be in a sheet-like form, and may be wrapped around the implant to achieve coating.

Most preferably, an integrated orbital implant is used with a synthetic coating material, wherein said synthetic coating material causes no undue immune reaction in the patient, is absorbed by the patient, and is capable of being vascularized. Particularly, an integrated orbital implant comprised of sterile, low density, porous hydroxyapatite, with sterile coating material including at least one synthetic polymer is the most preferred embodiment. As described herein, Plaster of Paris is a preferred coating material, since it serves to smooth over orbital implants without the adverse effects described above.

As will be described in further detail below, the coating material may be comprised of synthetic material which is also useful to deliver therapeutic agents, such as vascularization agents. For example, the synthetic material may be a polymer cross-linked in such a way as to provide for time-released drug delivery. The cross-linkages may essentially "trap" aqueous solutions of therapeutic agents, and substantially mediate the release of such agents from the coating materials. Other means of incorporating therapeutic agents into coating materials will be apparent to those skilled in the art.

Therapeutic agents, in addition to agents which promote vascularization, may also include, for example, antibiotic agents, wound healing promoters, blood clotting/blood clot dissolving agents, or mixtures thereof.

Smooth-Coated Hydroxyapatite Implants:

One reason for having a smooth surface on an hydroxyapatite orbital implant is primarily to allow it to be placed into the socket without the surface of the hydroxyapatite orbital implaht grabbing onto the soft orbital tissues. The surface of the hydroxyapatite orbital implant is covered with many small spicules, and it is very much like VELCRO™; when placed in contact with soft tissue—it clings to the tissue very firmly Therefore, without having a smooth surface, the hydroxyapatite orbital implant cannot easily be placed deep within the orbit.

Coating or wrapping the hydroxyapatite orbital implant in homologous sclera makes the outside surface smooth and allows the implant to go into the orbit in a way similar to a silicone or plastic ball. If it is not wrapped in sclera, the implant can be wrapped with two pieces of thin plastic; accordingly, once the implant was in place, the plastic was withdrawn from the orbit, leaving the hydroxyapatite orbital implant in its proper position in the deep orbit.

An hydroxyapatite orbital implant with a smooth coating on the outside that is absorbable makes it easy to place the implant deep within the orbital tissues without separately coating or wrapping it in any other material. For example, Plaster of Paris, when used as a coating directly over the hydroxyapatite implant, smooths the surface of the implant and allows for deep orbital implantation. In addition, Plaster of Paris is absorbed and allows for penetration of fibrovascular tissue, and avoids immunoincompatability problems. Also, Plaster of Paris is autoclavable, and inexpensive. Other coatings which are calcium-based or otherwise similar to Plaster of Paris may also provide these advantages. The description of combining the coatings with other materials, such as therapeutics, may also be applicable herein.

Other coatings which provide for a smooth surface, which are capable of being absorbed or penetrated with fibrovascular tissue and which provide no significant immunoincompatability problems will be apparent to those skilled in the art.

Vascularization Agents/Therapeutic Methods:

Relatedly, as indicated above, agents which promote vascularization may also be used in conjunction with orbital implants, particularly integrated orbital implants. Generally, the term "promote" with reference to vascularization denotes increasing the rate of blood vessel formation, or increasing the number of blood vessels per unit volume. Typically, the more that vascularization was promoted, the sooner the orbital implant was integrated into the patient's orbital socket. Even if integrated orbital implants are not used, improved vascularization in the area surrounding the implant may promote wound healing.

One advantage of having the hydroxyapatite orbital implant impregnated with an agent that causes more rapid vascularization is that the patient can be fit with a prosthesis sooner, since the implant has vascularized more rapidly.

The motility peg should not be placed within the implant until there is good vascularization of the implant. Such vascularization took approximately six months in most patients and even longer in a small number of patients. Once the hydroxyapatite orbital implant was impregnated with fibrovascular tissue, the chances of implant migration were much decreased, as was the chance of it becoming infected.

Other porous implants, in addition to hydroxyapatite orbital implants, are also suitable, and may be vascularized. Preferably, the pores will be interconnected, i.e., the pores will not "dead end." This leads to full vascularization.

Increase in vascularization may be accomplished by vascularization agents, such as growth factors. These growth factors may be applied via the orbital implant itself, for example, by dipping the orbital implant into a solution containing the vascularization agent prior to insertion of the orbital implant. Alternatively, as described above, the vascularization agent may be incorporated into the coating or wrapping material. For example, if a synthetic polymer is used, the polymer may be prepared such that the vascularization promoter is contained within the chains of the polymer molecules. Another alternative is for the implant to be impregnated with a vascularization agent as part of the manufacturing process.

As yet another alternative, exogenous vascularizing agents may be applied as a post-operative therapy to encourage the integration of an integrated orbital implant or promote wound healing. One skilled in the art will envision other means for applying vascularization agents in this context to improve the rate or character of vascularization of the orbital implant.

Examples of agents which promote vascularization include growth factors, such as epidermal growth factor, fibroblast growth factor, neovascular growth factor, and epithelial growth factor. Also, serum or plasma, preferably from the patient himself to avoid antigenicity or disease transmission problems promotes vascularization. One skilled in the art will be able to ascertain other useful vascularization agents.

These agents which promote vascularization may also be used in conjunction with other agents which produce beneficial effects. For example, immunosuppressant or antibiotic agents may provide beneficial results and prevent undue immune response or insure against undue infection. Certain cell-adhesion modulating molecules, such as arginine-glycine-aspartic acid (RGD) containing compounds, or heparin may provide beneficial cell adhesion to the implant and thereby promote integration of integrated implants.

It should also be understood that vascularization agents may be contained in an impure medium or may be contained as a mixture of known ingredients. For example, it has been thought that dipping a hydroxyapatite integrated orbital implant into the patient's own normal human serum or plasma increases the rate and the degree of robustness of the vascularization. One skilled in the art will recognize that there are many vascularizing agents, some of which may also function as wound healing agents, or have other beneficial functions. The above list of vascularization agents is not intended to be complete, and it is not intended to provide limitation to the appended claims. For example, in the practice of the therapeutic methods of the present invention, an effective amount of the active compound, including derivatives or salts thereof, or a pharmaceutical composition containing the same, is administered via any of the usual and acceptable methods known in the art, either singly or in combination with another compound or compounds of the present invention or other pharmaceutical agents such as immunosuppressants, antihistamines, corticosteroids, and the like.

These compounds or compositions can be administered orally, sublingually, topically (e.g., on the skin or in the eyes) parenterally (e.g., intramuscularly, intravenously, subcutaneously or intradermally), or by inhalation, and in the form of either solid, liquid, or gaseous dosage including tablets, suspensions, and aerosols, or other forms. The administration can be conducted in single unit dosage form with continuous therapy or in single dose therapy ad libitum. As described above, the compounds also may be delivered via the implant coating or wrapping material, or via the implant itself.

In one preferred embodiment, the therapeutic methods of the present invention are practiced when the relief of symptoms is specifically required or perhaps imminent; in another preferred embodiment, the method herein is effectively practiced as continuous or prophylactic treatment.

In the practice of the therapeutic methods of the invention, the particular dosage of pharmaceutical composition to be administered to the subject will depend on a variety of considerations including the nature of the affliction, the severity thereof, the schedule of administration, the age and physical characteristics of the subject and so forth. Proper dosages may be established using clinical approaches familiar to those skilled in the medicinal arts.

Size of an Orbital Implant:

Purposes of an orbital implant comprise: to prevent retraction of orbital tissues, to replace the volume lost by the removal of the eye, to help the prosthesis fit more comfortably and more accurately, and to produce movement of an artificial eye prosthesis. Replacing the volume of the orbit has a major effect on the final appearance of the artificial eye.

The volume of the artificial eye plus the volume of the orbital implant should be equal to the volume of the eye that was removed. If the eye is assumed to be a sphere with a diameter of 24 mm, the volume of that sphere is 7.2 cc (v=4 πR/3). The average artificial eye has a volume of 2.5 cc. Therefore, the volume of the orbital implant should be the difference between the volume of the eye removed (7.2 cc) and the volume of the artificial eye (2.5 cc). This calculation results in an implant that should supply a volume of 4.7 cc (7.2 cc–2.5 cc). An implant that supplies this volume would have a diameter of 21 mm. Table 1 shows the volume of various implant sizes and the approximate implant sizes to use with eyes of different diameters.

In the past, ophthalmologists have been taught that the largest implant that should be used following an enucleation was 18 mm. It was thought that an implant larger than 18 mm was more likely to be closed with tension on the Tenon's and conjunctival suture line, and therefore, the wound would more likely break down and the implant extrude. The recommended sizes of orbital implants therefore were usually 16 mm or 18 mm. With the use of an 18 mm sphere, a volume deficit of 1.4 cc would occur. The use of a 16 mm sphere will produce a volume deficit of 2.3 cc. Volume deficits of 1.4 cc–2.3 cc correspond very well clinically to the volumes often needed to correct enophthalmos with subperiosteal orbital volume augmentation.

Formerly, clinicians may have found the rate of extrusion to be higher with implants larger than 18 mm because implants were placed primarily within Tenon's capsule. With a small opening in posterior Tenon's and the implant placed within the confines of Tenon's capsule, an implant larger than an 18 mm did put undue tension on the anterior Tenon's closure.

Soll made a great contribution in surgical technique with his recommendation of placing the implant within the muscle cone posterior to the deep layer of Tenon's capsule (D. B. Soll, *Archives of Opthal.* (1972) Vol. 87, p. 196. This allowed a larger implant to be placed in the orbit and still have Tenon's capsule closed without tension. Generally, in an adult a 20 mm or 22 mm sphere can easily be placed in the muscle cone and Tenon's be closed without tension.

A large implant (e.g., 22 mm) will be needed if prior to the enucleation a patient has had several surgical procedures or for any other reason may have had retraction or fibrosis of the orbital soft tissues, or had fat atrophy. Wrapping an implant in eyebank sclera adds about 1.5 mm to the diameter of the implant. Therefore, a 20 mm sphere wrapped in eyebank sclera gives a volume of a sphere with a diameter of 21.5 mm. For sclera-wrapped implants, a 20 mm or 22 mm PHA implant wrapped in sclera was used in almost all adults with normal-sized globes. Similar techniques can be used for measuring the volume and diameter of implants coated or wrapped in other material.

Further complications, in addition to extrusion, can result from placing an orbital implant that was too large into the orbit. One problem is that the ocularist may not be able to fit an artificial eye with enough anterior—posterior thickness to create a realistic anterior chamber depth. Also, there may not be enough thickness to allow the ocularist to later drill the posterior surface of the prosthesis to create the socket for the peg. When the prosthesis must be made thin to prevent a proptotic appearance, the anterior chamber depth is shallow, and the iris diaphragm appears to be bowed forward. This gives less than a satisfactory result. For example, this is one of the primary problems with the appearance of a type of artificial eye commonly referred to as a scleral shell, an artificial eye which is used to cover a blind cosmetically unacceptable eye.

If this situation were to occur with a porous hydroxyapatite (PHA) spherical implant, the problem would be solved by making an incision over the implant and exposing the implant material. A small drill can then be used to bur away the anterior portion of the implant material and its investing soft tissue. The soft tissue anterior to the implant can then be closed and the volume of the implant reduced. Also, vascularizing materials can be added at this point.

The examples set forth above are illustrative, and are not to be construed as limitations of the appended claims. One skilled in the art will recognize other embodiments of the present invention.

TABLE 1

DETERMINATION OF ORBITAL IMPLANT SIZE

| (A) EYE SIZE | (B) EYE VOLUME | (C) PROSTHESIS VOLUME | (D) VOLUME TO BE REPLACED | (E) IDEAL IMPLANT SIZE |
|---|---|---|---|---|
| 22 mm | 5.6 cc | 2.5 cc | 3.1 cc | 18 mm |
| 23 mm | 6.4 cc | " | 3.9 cc | 19–20 mm |
| 24 mm | 7.2 cc | " | 4.7 cc | 21 mm |
| 25 mm | 8.2 cc | " | 5.7 cc | 22 mm |
| 26 mm | 9.2 cc | " | 6.7 cc | 23 mm |

Drilling a Hole in the Implant:

The patient that received a porous hydroxyapatite (PHA) orbital implant was treated in the same way as any other anophthalmic patient postoperatively. There may be slightly more swelling in the early postoperative period because of the movement of the implant in the socket. With integrated implants, the socket was usually ready for a custom-fit prosthesis in six weeks.

Integrated implants were drilled after they came to contain fibrovascular tissue. The time for implant vascularization was variable. Even though wrapping an implant is advantageous, an integrated implant vascularizes more quickly if not wrapped. Similarly, the time it takes for sclera to be resorbed is variable. See, e.g., D. B. Soll, *Advances in Ophthalmic, Plastic and Reconstructive Surgery*, Vol. 2, p. 1322, St. Louis, C. V. Mosby Co (1987). Having openings cut in the covering of sclera or other appropriate coating or wrapping material, increases the rate of vascularization. If left completely wrapped in sclera, the implant was generally vascularized in about six months. It is likely that other coating or wrapping material, such as synthetic collagen, will require a similar time frame for vascularization in the absence of vascularization agents. And, as indicated above, vascularization agents can be used to improve the time frame for vascularization.

Figure 2:
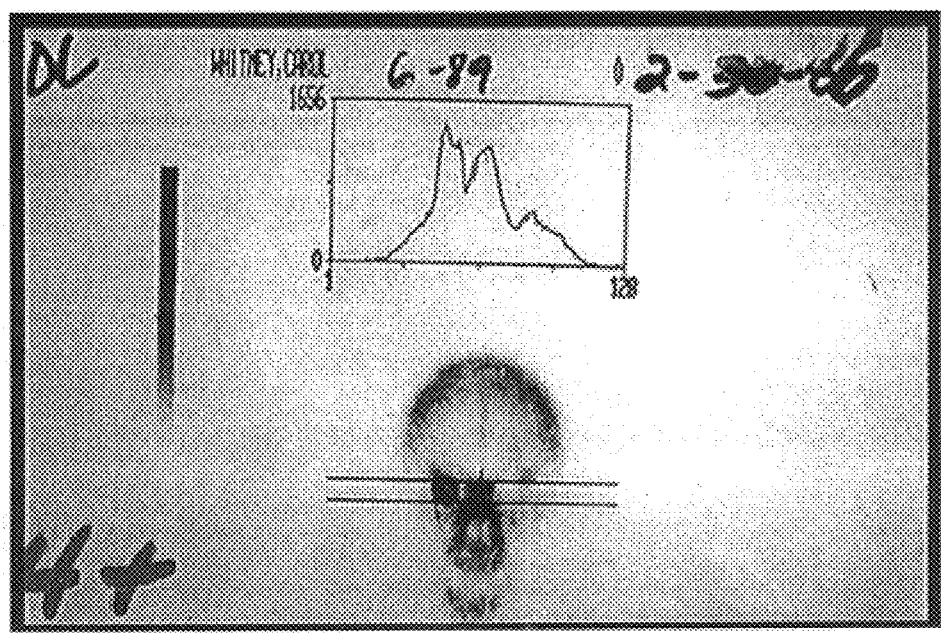
FIG. 2 is a technetium$^{99}$ bone scan showing good uptake and hence good vascularization of the implant in the right orbit.

At about six months postoperatively, a technetium$^{99}$ bone scan was done to assess the vascularity of the implant (FIG. 2). If the implant was well vascularized, it was ready to be drilled or otherwise made into a direct motility implant. One skilled in the art will be able to ascertain the degree of vascularization.

The drilling of a hole for the motility prosthesis (e.g., an artificial eye and a motility peg) was done under retrobulbar (actually retroimplant) local anesthesia. The area on the surface of the conjunctiva to be drilled was marked with a marking pen. This location was most easily determined by having the ocularist make a template of the patient's artificial eye. In the area of the pupil, the template has a through-and-through hole. By placing the template in the socket, the surface of the conjunctiva can be marked through this hole. This indicates the correct location for drilling.

Once the area for drilling has been determined, the eye was prepped and draped in the usual fashion. A lid speculum was placed between the lids, and the area to be drilled was cauterized with a hand-held cautery, presently the drilling procedure is performed without cautery. The conjunctiva and sub conjunctival tissues were grasped with heavy-toothed forceps to stabilize the implant; presently an implant ring stabilizer (Integrated Orbital Implants, San Diego, Calif.) is used to stabilize the implant. A hole 3 mm in diameter and 10–13 mm in depth was drilled. It has been found to be preferable to use a drill bit with the cutting portion limited only to the end of the bit and not extending up the sides of the bit. This avoids the conjunctiva from being gathered up onto the drill bit.

Figure 3:
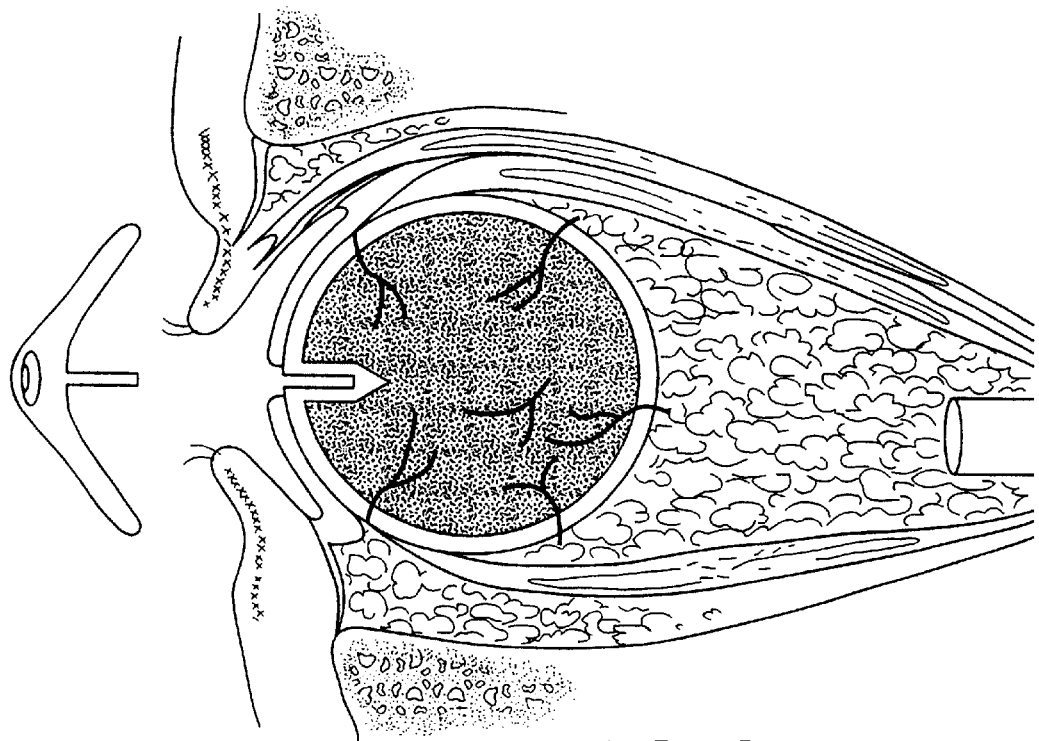
FIG. 3 is a schematic representation of an implant showing a peg for direct attachment of an artificial eye.

A flat-headed peg 2.5 mm in diameter and 10 mm long was placed in the drilled hole. If the fit was good and the peg seated well against the conjunctiva, the peg was removed, the hole was irrigated, the peg covered with antibiotic ointment and replaced in the hole. The patient's artificial eye was replaced over this, and the eye was patched for 24 hours. In three to four weeks, the patient was sent to an ocularist to have this peg fit to the posterior surface of the artificial eye (FIG. 3). In certain peg embodiments, such as a threaded peg, predrilling is not necessary before inserting the peg in the implant.

It cannot be emphasized too strongly that the closure of anterior Tenon's and conjunctiva was especially important if the PHA implant was not wrapped in sclera or some other material making a smooth surface. With the amount of movement that the implant will have by being attached to the extraocular muscles, without good closure the tissue may be broken down by the rough edges of the implant material.

Once the implant has been integrated with the fibrovascular tissues of the orbit, exposure of the implant during drilling was possible because the integrated implant supported fibrovascular and epithelial growth on its surface which helped to avoid infection.

In alternative embodiments for drilling the hole, a hole was drilled with dimensions, e.g., of approximately 0.5–6.0 mm in diameter, usually 2.5 to 5.0 mm in diameter. The length of the peg hole varies depending on the peg embodiment employed. Generally, if the peg was to protrude from the implant and engage the artificial eye, the hole was shorter than the length of the peg; if the peg comprises a recess that holds a stint that engages the artificial eye, the hole can be shorter, the same or longer than the length of the peg.

It is presently preferred that the hole be drilled all the way through the implant in order to facilitate circulation to the peg hole; threads on the outer surface of the peg can facilitate proper placement of a peg in such a hole.

In alternative embodiments, for a peg that either lacks a head or had a head that was no wider than the peg shaft, the hole was shorter than the length of the peg so that the peg protrudes from the hole; the hole for a ball-headed peg was usually at least as long as the shaft portion of the peg (the portion that does not constitute the ball head); usually the hole for a sheath-like peg embodiment was as long as or longer than the length of the peg.

Coupling the Integrated Implant to an Artificial Eye

Figure 4:
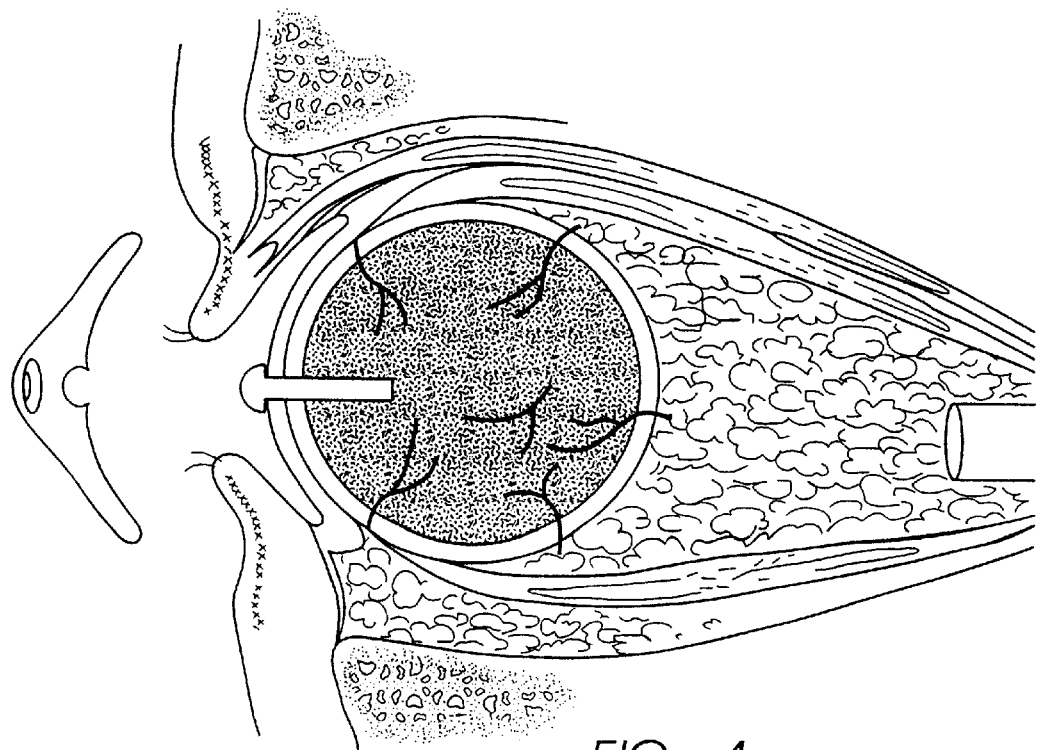
FIG. 4 is a schematic representation of an implant showing a "ball-and-socket" coupling/articulation/joint for direct attachment of an artificial eye.

The most common way an implant was coupled to an artificial eye was to have a flat-headed peg replaced with a peg 13 mm long that had a rounded area or ball on one end. The ball portion of the peg sits above the surface of the conjunctiva. The ocularist then drilled a small hemispherical indentation out of the back of the patient's artificial eye, and the ball of the peg fit into this socket. By this ball-and-socket coupling, the movement of the implant was transferred to the artificial eye (FIG. 4). Alternatively, the flat-headed peg was attached directly to the posterior surface of the artificial eye. Permanent attachment was most frequently used when an implant was too large and the corresponding artificial eye was too thin to have a recess drilled on its posterior surface.

The following principles were used when selecting the size of a peg: the diameter should be large enough so as not to break; if the material from which the peg is constructed is pliable, the diameter should be sufficiently large so that the peg does not bend unduly, which could cause the peg to be difficult to insert into the peg hole; the diameter should not be so small so as to make it hard to place or replace in the patient's orbit.

Where a peg was to be placed in a hole, the hole was irrigated, the peg was coated with antibiotic ointment was placed in the hole. FIG. 5 depicts a sheath-like peg embodiment placed in a hole.

Typically, the external surface of the sheath-like peg had threads to facilitate screwing into a drilled hole. In certain threaded peg embodiments, the threads permit the peg to be placed into the implant without the need for a predrilled hole. Threaded peg embodiments are preferred because they allow the physician to adjust the level of the peg relative to the surface of the artificial eye, and the threads are believed to help prevent extrusion of the peg upon tissue ingrowth.

Accordingly, after coating the peg, such as that of FIG. 5, with antibiotic the threaded peg was screwed to a level approximately 2–3 mm beneath the surface of the conjunctiva. A temporary stint was placed in the cavity of the peg. After healing was allowed for approximately four weeks, the temporary stint was replaced with a ball headed stint, where the ball of the stint was capable of mating with a complementary recess on the posterior surface of an artificial eye, to create a ball-and-socket joint when the artificial eye was in place.

In the embodiment depicted in FIG. 6, the artificial eye 28 is coupled to a sheath-like embodiment of peg 20 by a stint 26. The stint was configured to fit in the cavity 24 defined by the peg, as seen in FIG. 5. Preferably, the distal end of the stint permitted rotation of the artificial eye around a longitudinal axis of the stint, and more preferably permitted movement in three dimensions relative to a pivot point generally located on the longitudinal axis of the stint. Accordingly a smooth convex surface such as a ball was formed on the distal end of the stint; the convex surface mated with a corresponding concave indentation on the posterior surface of the prosthesis to create a "ball-and-socket" coupling. As disclosed herein, a "locking" ball-and-socket is particularly preferred.

The implant-prosthesis coupling embodiment comprising a sheath-like peg is presently preferred, in that the insertion and removal of the stint does not cause undue trauma to the ocular tissues. The surfaces regularly contacted during stint insertion and removal are not living tissue, and trauma to living tissue is avoided, as is breakdown of the hydroxyapatite at the outer/upper margins of the peg hole. Other advantages of a sheath-like peg include that peg hole patency is assured, and it is more comfortable for the patient when the peg is inserted. Advantageously, the sheath-like peg can still be removed from the eye if necessary.

EXAMPLES

Surgical Technique—Enucleation

Enucleation is the complete removal of the eyeball after severing it from the eye muscles and the optic nerve. This example describes the surgical technique of enucleation and replacement of the contents in the orbital socket with a hydroxyapatite implant. Coatings and wrappings are discussed.

The enucleation procedure may be done under local or general anesthesia. In either case, 4–5 cc of 2% Lidocaine with epinephrine and Hyaluronidase were given in the retrobulbar space for hemostasis. When local anesthesia was used, the 2% Xylocaine with epinephrine was optionally mixed as a 50—50 mix with 0.75% Bupivacaine and Hyaluronidase to achieve a longer duration of effect. A 4-0 silk double-armed suture was used through the upper fornix in a mattress fashion (D. B. Soll, *Archives of Opthal.* (1972) Vol. 87, p. 196). This was done to isolate and protect the levator muscle and to identify the superior fornix to keep it from being shortened during closure of anterior Tenon's capsule. In cases of secondary implant, this suture may also be used inferiorly to delineate the desired inferior fornix. A 360-degree peritomy was done preserving as much conjunctiva and Tenon's as possible. The extraocular muscles, including the obliques, were tagged with a double-armed 5-0 Vicryl suture, and the muscles were released from the globe. The neurectomy was done according to the surgeon's preference, and the eye was delivered. As in any enucleation procedure, hemostasis should be well-controlled prior to putting an implant in the socket.

At this point, the hole in posterior Tenon's capsule was evaluated where the optic nerve penetrated the capsule. If this opening was small, it was widened by spreading the opening with a blunt hemostat. This allowed the orbital implant to extend into the muscle cone, thus allowing a larger implant to be used. It was then possible to close Anterior Tenon's layer without tension. This is a variation on the technique first described by Soll (Id). In the technique described therein, however, posterior Tenon's capsule was not closed anterior to the implant.

The size of the porous hydroxyapatite (PHA) orbital implant to be used was then determined by placing a silicone or acrylic sphere into the orbit. Generally, a 20 mm or 22 mm sphere easily fit into the orbit with anterior Tenon's capsule being pulled together without tension. By evaluating the fit of the silicone or acrylic sphere, the size of the PHA sphere to be used could be chosen. If one used sclera to wrap the implant, this added 1.5 mm in diameter to the implant. Therefore, if one determines with the acrylic sizing sphere that a 22 mm implant fits well, a 20-mm PHA sphere wrapped in sclera would be its equivalent.

If sclera was to be used, it was soaked in a saline and antibiotic solution (e.g., 30 cc of saline with 80 mg of Gentamycin). A selected PHA implant was soaked in the same solution. If the sclera has been preserved in alcohol or glycerin, these substances should be entirely removed and the sclera completely hydrated before soaking it in the antibiotic and saline solution. The PHA implant was placed in this scleral shell, and the sclera was sutured around the sphere with 5-0 Vicryl. The sclera was trimmed to fit snugly around the implant. When using sclera, it was preferred to use a whole-eviscerated eyebank globe treated in alcohol and preserved by treating it in a solution of saline and Gentamycin (e.g., 100 cc of saline and 40 mg or Gentamycin) and freezing it. As for using sclera, it is preferred to use sclera to wrap the PHA implant as opposed to placing it in the socket unwrapped.

Experience has shown that the movement of the implant and thus the artificial eye was greater when the implant was coated or wrapped. The use of other wrapping or coating materials is herein described. Procedures for using bio-polymers or other materials described herein may be performed prior to the initiation of surgery, if these materials are not rapidly degraded. For example, the entire step of wrapping the implant in sclera is eliminated if the implant is coated with Plaster of Paris. For using bio-polymers, for example, one may essentially coat or wrap the implant in a material comprised of the bio-polymer. This may be done in advance of the surgery, and obviate the need for prolonging the patient's exposure to anesthetics.

In addition, the implant itself may be impregnated with vascularizing agents at this point or previously. For example, the implant may be dipped in the patient's own serum, or other vascularizing agent, prior to surgery. As described above, the vascularizing agent may be in the coating or wrapping material, as well as the implant itself.

For example, an hydroxyapatite orbital implant may be coated in Plaster of Paris, autoclaved, and ready for insertion into the recipient. Alternatively, an hydroxyapatite orbital implant may be dipped in a bio-polymer, or dipped in a "cocktail" of biopolymer, therapeutic agent (such as antibiotic), and vascularization agent. Alternatively, an hydroxyapatite orbital implant may be dipped in a vascularization agent, then wrapped in a sheet-like form of a biopolymer, such as a suitable size sheet of collagen which has been prepared in vitro. These examples are illustrative, as a wide variety of combinations may be selected, which selection may depend on the recipient, the surgeon's own experience, and the materials involved, as well as other factors which will be apparent to one skilled in the art.

Once the PHA implant has been coated or wrapped in sclera or other material, the anterior pole of the implant was determined and marked with a marking pen (typically an area near the former penetration of the optic nerve through the sclera). Moreover, the cornea was often removed from the sclera and the resulting scleral hole placed in the posterior portion of the socket. The area where the rectus muscles were to become attached to the sclera was then determined, and small windows (5 mm×7 mm) of sclera were cut out (FIG. 1). This area of attachment could be determined by placing the scleral wrapped implant into the orbit in its proper position and marking where the cut ends of the rectus muscles fall on the sclera with normal tension being placed on the muscles. The rectus muscles were then sewn to the sclera by passing the double-armed 5-0 Vicryl through the anterior lip of the scleral window. Tying the suture down snugly pulled the muscle into the window and into contact with the PHA sphere. Optionally, the obliques were attached at their appropriate positions on the sclera, but windows were not generally cut out for their attachment.

Cutting out the windows in the sclera for the attachment of the muscles and cutting the cornea out and placing it posteriorly, allowed more rapid vascularization of the PHA implant. Blood vessels can more rapidly go into the PHA material without having to first penetrate the sclera.

Optionally, the double-armed sutures anchoring the rectus muscles to the sclera were then be passed through anterior Tenon's and conjunctiva into their respective fornices and tied externally on the conjunctiva. This tended to deepen the fornix. Care should be taken to place these sutures in such a fashion that they do not keep anterior Tenon's capsule and conjunctiva from closing without tension. The anterior Tenon's layer was then closed with interrupted 5-0 Vicryl suture, and the conjunctiva was closed with a running 5-0 Vicryl suture. Antibiotic ointment was applied to the socket and an acrylic conformer was placed in the socket. Care was taken to be sure the conformer did not put undue pressure on the closure of conjunctiva and Tenon's capsule. One or two inter-marginal temporary tarsorrhaphy sutures of 5-0 Vicryl were optionally used if more than normal edema was anticipated. These intermarginal sutures were routinely used with eviscerations. At the end of the procedure, 4 cc of 0.75% Bupivacaine were injected into the muscle cone for postoperative pain control.

A firm pressure dressing was typically placed over the orbit, and was left in place for 4–5 days. The patient typically was placed on an oral antibiotic for ten days. A four-day course of oral steroids was optionally used to decrease the swelling of the orbit and therefore decrease the patient's discomfort. After the dressing was removed, the socket was treated with topical antibiotics, and the socket was usually ready for a prosthetic fitting in six weeks.

In one variation, prior to implantation holes were cored through the implant material with a 19-gauge hypodermic needle and a 4-0 Vicryl suture passed through these holes with a Keith needle. The extraocular muscles were then tied to the 4-0 Vicryl suture material that has been passed through the implant.

The PHA implant optionally may be placed in the enucleated socket without being wrapped ip sclera or other permanent wrapping. Smooth material may be used to drape the rough implant for insertion. Once inserted, the smooth material may be removed. When sclera was not used, two pieces of plastic draping material slightly overlapped on each other were typically used. The PHA sphere was placed in the center of this overlapped plastic, and the edges of the plastic were drawn up around the implant. The implant then being completely wrapped in this plastic material was then capable of being placed into the deep portion of the orbit. The index finger holds the orbital implant in place, and the two pieces of plastic were gently pulled from underneath the implant leaving the implant in its proper position. Tenon's capsule and conjunctiva were then closed over the implant in a normal fashion.

Since the material has a rough surface and has many small spicule-type projections, when not wrapping the material in sclera or otherwise providing for a smooth surface, extra care should be taken in closing the Tenon's and conjunctiva because the sharp edges of the material may cause the anterior closure to open. If there was any question as to the integrity of the anterior closure, a small cap of sclera or fascia can be placed between the anterior surface of the implant and the Tenon's closure. This gives another barrier of protection and prevents early exposure. Until this implant becomes vascularized, it should be treated as any other implant, and early exposure should be avoided.

Surgical Technique—Evisceration

The porous hydroxyapatite implant is well-suited to be used with an evisceration. Accordingly, an implant was placed within the patient's own sclera. The implant to be placed within the patient's own sclera is optionally coated or wrapped prior to insertion in the scleral cavity.

Evisceration, the removal of the intraocular contents of the eye, can be done with the cornea left intact, or with the cornea removed. The procedure was done under a local or general anesthesia. After the appropriate anesthesia had been given, a lid speculum was placed between the lids and a 360 degree peritomy of the conjunctiva was done at the limbus. If the cornea was to be removed, it was removed at this time and a dissection carried out between the choroid and the sclera to remove the intraocular contents. The intraocular contents may be saved as a surgical specimen for examination by pathologists.

If the cornea was left intact, an incision in the sclera approximately 5 to 6 mm. posterior to the limbus just in front of the insertion of the superior rectus muscle was carried out and extended for 180 degrees. The intraocular contents were removed with an evisceration spoon with the dissection being carried out between the sclera and choroid. This specimen was also sent for a pathology evaluation.

The inside layer of the sclera was scrubbed well to remove any further residue pigment. Also, if the cornea was left intact, the epithelium and the endothelium, were removed. The inside of the sclera was then treated with a cotton tip applicator soaked in absolute alcohol to denature any remaining pigmented calls. The inside of the sclera was well irrigated with normal saline solution. Hemostasis was maintained with a cautery unit.

Relaxing incisions in the sclera were optionally made in-between the rectus muscles to allow a larger implant to be placed within the scleral cavity. Also, the sclera could be opened posteriorly to allow a larger implant to be placed within the scleral cavity and also, by opening the sclera in the posterior aspect, this allowed more rapid vascularization of the hydroxyapatite implant. The scleral cavity was sized with a silicone or plastic sphere to determine the size of the hydroxyapatite implant. Once the size was determined, the hydroxyapatite implant was placed on the sterile table and soaked in antibiotic solution and saline.

If the implant was not coated, the hydroxyapatite implant was then wrapped in two pieces of thin draping plastic. This was done by placing two 6×6 inch pieces of plastic so that the edges overlapped by ¼ inch. The hydroxyapatite implant which had been chosen was placed in the central portion of this overlapped area, and the plastic was drawn up around the hydroxyapatite implant. This produced a smooth coating for the outside of the implant.

If the implant is already coated with another material, as described above, this would not be necessary. Also, as indicated above, the implant or coating may be treated with vascularization agents or other therapeutic agents. As described above, the implant may be coated or wrapped in synthetic material, such as Plaster of Paris, or biopolymers, and vascularizing agents may be used, for example, in conjunction with antibiotics. This prepared implant is then inserted into the sclera.

The implant was then placed within the scleral cavity and if the plastic had been used, the plastic was pulled out from under the implant while the implant was being held in the scleral sac with the index finger. The sclera anteriorly was then closed with interrupted 5-0 Vicryl sutures. Tenon's capsule was then closed over the sclera and/or cornea with interrupted 5-0 Vicryl sutures and then the conjunctiva was closed with a running 5-0 Vicryl suture. A temporary conformer was placed within the lids after antibiotic ointment had been applied, and the lids were temporarily closed with two tarsorrhaphy sutures of 5-0 Vicryl. A firm pressure dressing was then applied.

Surgical Technique—Secondary Orbital Implant

The porous hydroxyapatite orbital implant can be used as a secondary implant in patients who have (1) no orbital implant, (2) a migrated orbital implant, (3) an implant with inadequate volume, (4) an extruding orbital implant, or (5) in patients who desire to have more motility of the artificial eye. This procedure can be done under local or general anesthesia.

Accordingly, after adequate anesthesia had been given, a double-armed silk suture was placed in the upper and lower fornix to identify the fornices. A lid speculum was placed between the lids. An incision across the posterior aspect of the orbit was made in the horizontal dimension. A conjunctival flap was dissected into the fornix above and below. The orbital implant and its pseudocapsule were removed, if they were present, and a pocket for the new orbital implant was fashioned. The orbital implant could then be placed into this pocket, wrapped in sclera or unwrapped. If the implant surface is smooth (such as if it is pre-coated), no wrapping is necessary. As with the surgical techniques above, the implant may be coated with a variety of materials, and may contain vascularization agents or other therapeutic agents. It should be noted that prior to implanting the hydroxyapatite implant, in this or other surgical procedures, it should be soaked in saline with antibiotic solution.

After placing the implant into the Bocket, the anterior soft tissues were closed with interrupted 5-0 Vicryl, and the conjunctiva was closed with a running 5-0 Vicryl. If the muscles were to be attached to the implant, after the patient's implant had been removed along with its pseudocapsule, exploration of the orbit was then done in an attempt to locate and isolate the extraocular muscles. Once these had been identified, the hydroxyapatite implant was placed into the orbit. The implant is optionally treated with coatings or vascularizing agents or other agents as described above.

The extraocular muscles were then sutured to the implant material or to the surrounding wrapping, such as if the implant is wrapped in sclera or wrapped in a synthetic coating which is in sheet form. After suturing the muscles to the implant, the anterior soft tissues were closed with interrupted 5-0 Vicryl and the conjunctiva was run with 5-0 Vicryl. A temporary conformer was placed between the lids after antibiotic ointment had been applied, and temporary tarsorrhaphy sutures of 5-0 Vicryl were applied. A firm pressure dressing was then applied.

What is claimed is:

1. An article for placement in the orbital cavity of a recipient, wherein said article comprises:
   an orbital implant sized and configured to be used in evisceration, enucleation and/or secondary orbital implant replacement wherein said orbital implant is covered by a bioabsorbable synthetic coating.

2. The article of claim 1, wherein the orbital implant is porous.

3. The article of claim 1, wherein the orbital implant comprises hydroxyapatite.

4. The article of claim 3, wherein said implant further comprises porous low density hydroxyapatite or granular high density hydroxyapatite.

5. The article of claim 1, wherein said orbital implant comprises a material selected from the group consisting of silicone, acrylic and a combination thereof.

6. The article of claim 1, wherein said synthetic coating comprises a means for reducing an adverse immune response by a recipient.

7. The article of claims 1, wherein said synthetic coating comprises a synthetic material comprising calcium.

8. The article of claim 7, wherein said synthetic material comprises a plaster of paris (2 $CaSO_4$, $H_2O$).

9. The article of claim 1, wherein said synthetic coating is prepared by an in vitro technique.

10. The article of claim 9, wherein said in vitro technique is selected from the group consisting of cell culture, recombinant nucleic acid technology, and a combination thereof.

11. The article of claim 1, wherein said synthetic coating comprises a polymer.

12. The article of claim 11, wherein said polymer comprises a material selected from the group consisting of polyglycolic acid, polylactic acid, polycaprolactone, polydiox-anone, polycyanoacrylate, polyorthoester, poly (gamma-ethyl glutamate), and pseudo poly (amino acid).

13. The article of claim 11, wherein said polymer is capable for timed release of a therapeutic agent.

14. The article of claim 13, wherein said timed release of a therapeutic agent comprises degradable polymeric cross-linkages.

15. The article of claim 1, wherein said coating comprises an extracellular matrix protein.

16. The article of claim 15, wherein said extracellular matrix protein is selected from the group consisting of collagen, fibrinogen, fibronectin, and vitronectin.

17. The article of claim 1, wherein said synthetic coating comprises material coated directly onto the orbital implant.

18. The article of claim 1, wherein said synthetic coating comprises material wrapped around the orbital implant.

19. The article of claim 1, wherein said synthetic coating comprises means for allowing a more rapid vascularization of the implant.

20. The article of claim 1, wherein said coating contains apertures that define windows there through said coating.

21. The article of claim 1, wherein said article further comprises a therapeutic agent.

22. The article of claim 1, wherein said orbital implant comprises a therapeutic agent.

23. The article of claim 1, wherein said synthetic coating comprises a therapeutic agent.

24. The article of claim 21, wherein said therapeutic agent is applied as a post-operative therapy.

25. The article of claim 24, wherein said post-operative therapy administration is selected from the group consisting of orally, sublingually, topically, parenterally, and by inhalation.

26. The article of claims 1, wherein said article comprises a therapeutic agent selected from the group consisting of a vascularization agent, an antibiotic agent, an immunosuppressant, a wound-healing promoter, a blood clot dissolving agent, a blood-clotting agent, a cell adhesion modulating molecule, and any combination thereof.

27. The article of claim 26, wherein said vascularization agent is an exogenous vascularizing agent.

28. The article of claim 26, wherein said vascularization agent is selected from the group consisting of a growth factor, a serum, and a plasma.

29. The article of claim 28, wherein said growth factor is selected from the group consisting of epidermal growth factor, fibro blast growth factor, neovascular growth factor, and epithelial growth factor.

30. The article of claim 26, wherein said vascularization agent is autologous or allogeneic.

31. The article of claim 26, wherein said cell adhesion modulating molecule comprising an arginine-glycine-aspartic acid (RGD) containing compound or heparin.

32. The article of claim 1, wherein said article further comprises an artificial eye.

33. The article of claim 32, which further comprises means for coupling the artificial eye to the orbital implant.

34. The article of claim 33, wherein said means for coupling the artificial eye to the orbital implant comprises a first magnetic pole in the orbital implant and a second magnetic pole in the artificial eye, said first magnetic pole and said second magnetic pole being oppositely poled.

35. The article of claim 1, wherein said implant defines a hole.

36. The article of claim 35, wherein said article further comprises a peg having a portion sized for placement within said hole.

37. The article of claim 1, wherein said article further comprises a peg configured to be coupled to said implant.

38. The article of claim 37, wherein said peg comprises means for coupling to the artificial eye.

39. A method for preparing an article for placement into the orbital cavity of a patient, said method comprises:

forming an orbital implant sized and configured to be used in evisceration, enucleation and/or secondary orbital implant replacement; and coating said orbital implant with a resorbable synthetic material.

* * * * *